(12) United States Patent
Turcott

(10) Patent No.: US 6,522,923 B1
(45) Date of Patent: Feb. 18, 2003

(54) METHODS, SYSTEMS AND DEVICES FOR OPTIMIZING CARDIAC PACING PARAMETERS USING EVOLUTIONARY ALGORITHMS

(75) Inventor: Robert Turcott, Mountain View, CA (US)

(73) Assignee: Pacesetter, Inc., Sunnyvale, CA (US)

(*) Notice: Subject to any disclaimer, the term of this patent is extended or adjusted under 35 U.S.C. 154(b) by 0 days.

(21) Appl. No.: 09/780,735

(22) Filed: Feb. 9, 2001

(51) Int. Cl.[7] .............................................. A61N 1/368
(52) U.S. Cl. ....................................................... 607/27
(58) Field of Search ................................ 607/9, 18, 27

(56) References Cited

U.S. PATENT DOCUMENTS

| | | | |
|---|---|---|---|
| 5,024,222 A | 6/1991 | Thacker ................ | 128/419 PG |
| 5,168,869 A | 12/1992 | Chirife ................ | 128/419 PG |
| 5,334,222 A | 8/1994 | Salo et al. .................... | 607/17 |
| 5,487,752 A | 1/1996 | Salo et al. .................... | 607/17 |
| 5,527,347 A | 6/1996 | Shelton et al. ................ | 607/9 |
| 5,540,727 A | 7/1996 | Tockman et al. .............. | 607/18 |
| 5,549,650 A | 8/1996 | Bornzin et al. ............... | 607/24 |
| 5,554,177 A | 9/1996 | Kieval et al. ................. | 607/17 |
| 5,626,620 A | 5/1997 | Kieval et al. ................. | 607/9 |
| 5,700,283 A | 12/1997 | Salo ............................ | 607/17 |
| 5,800,471 A | 9/1998 | Baumann ..................... | 607/25 |
| 5,836,987 A | 11/1998 | Baumann et al. ............. | 607/17 |
| 5,891,176 A | 4/1999 | Bornzin ....................... | 607/18 |

Primary Examiner—Scott M. Getzow
(74) Attorney, Agent, or Firm—Steven M. Mitchell

(57) ABSTRACT

Cardiac performance associated pacing parameters is improved by applying evolutionary algorithms that maintain a plurality of sets of pacing parameters for pacing a heart. An initial plurality of sets of pacing parameters are determined. A cardiac performance value is determined for each of the plurality of sets of pacing parameters. At least one set of pacing parameters is selected from the plurality of sets of pacing parameters based on the cardiac performance values. An updated plurality of sets of pacing parameters is then created based on the selected at least one set of pacing parameters. These steps (except for determining the initial plurality of sets of pacing parameters) are repeating a plurality of times, wherein each time the steps are repeated, the updated plurality of sets of pacing parameters most recently created are used. During performance of the above described steps the heart will be paced according to a plurality of different sets of pacing parameters that should all eventually evolve toward and be close to an optimum set of pacing parameters.

59 Claims, 8 Drawing Sheets

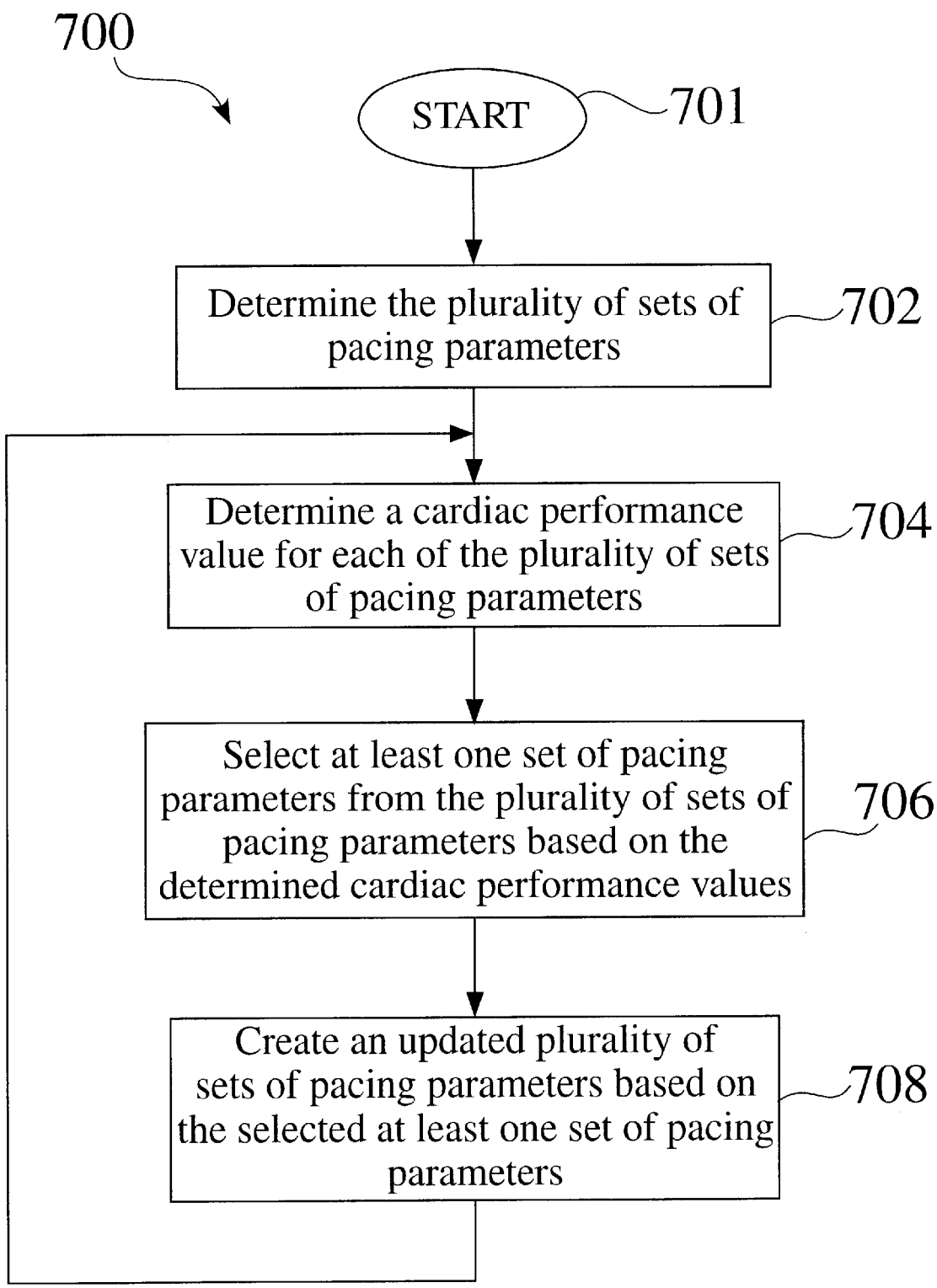

METHODS, SYSTEMS AND DEVICES FOR OPTIMIZING CARDIAC PACING PARAMETERS USING EVOLUTIONARY ALGORITHMS

BACKGROUND OF THE INVENTION

1. Field of the Invention

The present invention relates generally to implantable cardiac stimulation devices. The present invention more particularly relates to methods, systems and devices for adjusting cardiac pacing parameters to optimize pacing effectiveness.

2. Background Art

Implantable cardiac stimulation devices are well known in the art. Such devices may include, for example, implantable cardiac pacemakers and defibrillators either alone or combined in a common enclosure. The devices are generally implanted in a pectoral region of the chest beneath the skin of a patient within what is known as a subcutaneous pocket. The implantable devices generally function in association with one or more electrode carrying leads which are implanted within the heart. The electrodes are positioned within the heart for making electrical contact with the muscle tissue of their respective heart chamber. Conductors within the leads couple the electrodes to the device to enable the device to deliver the desired electrical therapy.

Traditionally, therapy delivery has been limited to the right side of the heart. However, new lead structures and methods have been produced and practiced for also delivering cardiac rhythm management therapy from or to the left heart. These lead structures and methods provide electrode electrical contact with the left atrium and left ventricle of the heart by lead implantation within the coronary sinus of the heart. As is well known, the coronary sinus passes closely adjacent the left atrium, extends into the great vein adjacent the left ventricle, and then continues adjacent the left ventricle towards the apex of the heart.

It has been demonstrated that electrodes placed in the coronary sinus and great vein may be used for left atrial pacing, left ventricular pacing, and cardioversion and defibrillation. These advancements enable implantable cardiac stimulation devices to address the needs of the wide patient population, from those that would benefit from right heart side pacing alone, to those that would benefit from left heart side pacing in conjunction with right heart side pacing (bi-chamber pacing), to those that would benefit from left heart side pacing alone.

The potential of multi-site pacing to improve the hemodynamic status (also referred to as cardiac performance) of select patient populations is well established in the research community. One area of active research is in determining optimal ventricular pacing configurations. For example, the results of one study suggest that optimal results are obtained by pacing on the side of the heart that has the conduction delay, so that left ventricular pacing gives superior performance for patients with a left bundle branch block, while right ventricular pacing yields better results in patients with right bundle branch block. As illustrated by those who conducted this study, the problem is typically couched in terms of pacing mode, so that comparison is made among right ventricular pacing, left ventricular pacing, and simultaneous bi-ventricular pacing. Unfortunately, this approach considers only a small subset of the parameter space, and therefore carries the risk of missing altogether the optimal pacing configuration (also referred to as the optimum pacing parameters).

Thus, there exists the further challenge, with multi-site pacing, of identifying the optimal pacing configuration (i.e., determining optimal pacing parameters). This challenge is complicated by the fact that only a limited region of the left ventricle is accessible for pacing, particularly when access is obtained via the coronary venous system.

A further challenge in multi-site pacing is that the number of potential pacing parameter combinations increases rapidly as the number of sites paced increases, making it that much more difficult to determine optimal pacing parameters. This problem can be formulated in terms of an abstract mathematical space, where each dimension of the space represents an adjustable independent pacing parameter. For example, in dual-chamber pacing (e.g., right atrium and right ventricle pacing) there is a single independent parameter, the atrioventricular (AV) delay (assuming a fixed pacing rate), and cardiac performance is a function of this parameter. In three chamber pacing (e.g., right atrium, right ventricle and left ventricle) there are two independent parameters (AV delay and interventricular RV-LV delay), and thus a two dimensional parameter space (assuming a fixed pacing rate). This can be generalized to any number of dimensions. For example, the parameter space of a four-chamber pacemaker would have three dimensions (assuming a fixed pacing rate). If pacing rate is also being analyzed then another dimension is added.

Although not efficient, an exhaustive search of a one dimensional parameter space (e.g., when two-sites are being paced with a fixed pacing rate) is possible, as shown in U.S. Pat. No. 5,540,727. However, as the number of sites (and thus, parameters) increases, an exhaustive search of parameter space quickly become unworkable, as illustrated in the following table.

| # of sites | # of dimensions | # of test points per dimension | time average per test point | total time for an exhaustive search |
| --- | --- | --- | --- | --- |
| 2 | 1 | 10 | 5 sec | 50 sec |
| 3 | 2 | 10 | 5 sec | 8 min |
| 4 | 3 | 10 | 5 sec | 1 hour, 20 min |

Accordingly, there is a need for more efficient and effective methods, systems and devices for optimizing multiple pacing parameters.

An additional challenge in multi-site pacing is that the optimal pacing configuration is dependent on the physiologic state of the patient. In patients with Hypertrophic Obstructive Cardiomyopathy, for example, the degree of obstruction is dependent on posture. Thus, the optimal pacing configuration for a walking patient is likely to be different from what is optimal for a patient who is sedated and supine on the examination or operating table. Thus, there is a need for efficient and effective methods, systems and devices for optimizing pacing parameters, that can dynamically adapt to changes in the physiologic state of the patient.

Further, the optimal pacing configuration may change as the patient's myocardial state changes. Myocardial remodeling is associated with the progression or regression of heart failure. Such remodeling may depend on response to therapy, lifestyle changes, and age. As the heart remodels, the optimum sequence of activation may change. For example, in the acute phase of pacemaker implantation, left ventricular pacing may have been optimal for a given patient. Over weeks or months, the heart may remodel such that more synchronous bi-ventricular pacing becomes optimal. Thus, there is a need for efficient and effective methods, systems and devices for optimizing pacing parameters, that can dynamically adapt to changes in the myocardial state of the patient.

BRIEF SUMMARY OF THE INVENTION

The present invention is directed towards methods, systems and devices for improving cardiac performance associated with pacing parameters by applying evolutionary algorithms that maintain a plurality of sets of pacing parameters for pacing a heart.

A method of the present invention includes the step of determining an initial plurality of sets of pacing parameters. A cardiac performance value is determined for each of the plurality of sets of pacing parameters. At least one set of pacing parameters is selected from the plurality of sets of pacing parameters based on the determined cardiac performance values. An updated plurality of sets of pacing parameters is then created based on the selected at least one set of pacing parameters. These steps (except for determining the initial plurality of sets of pacing parameters) are repeating a plurality of times, wherein each time the steps are repeated, the updated plurality of sets of pacing parameters most recently determined are used. During performance of the above described steps the heart will be paced according to a plurality of different sets of pacing parameters that should all eventually be close to an optimum set of pacing parameters. This method can be explained in terms of parameter space using the following example.

Assume an initial population consists of M=16 points within a parameter space, where each point represents a set of N=2 pacing parameters (e.g., AV delay and RV-LV delay). Multisite pacing pulses are delivered to a heart according to the delays defined by each point in the population. For each point a hemodynamic variable (also referred to as a cardiac performance value) or surrogate is measured and stored. An updated population of points is then created based on one or more of the best performing points (i.e., based on one or more of the sets of pacing parameters resulting in the best cardiac performance). For example, the point (i.e., the set of pacing parameters) corresponding to the best cardiac performance value is selected along with the remaining points (i.e., sets of pacing parameters) that are within a specific region about the best point. Each of the remaining points is replaced with a randomized version of one of the best performing points. In one example, the updated population of points includes the best performing points and randomized versions of the best performing points that have replaced those points outside the specific region.

Multisite pacing pulses are then delivered to the heart according to the delays defined by each point in the updated population. For each point a hemodynamic variable (also referred to as a cardiac performance value) or surrogate is measured.

An updated population of points is then created based on one or more of the best performing points of the updated population of points, in a manner similar to that described above. The above described method can be repeated indefinitely, or until a specific criteria is satisfied. During performance of the above described method the heart will be paced according to pluralities of different sets of pacing parameters that should all eventually evolve toward a global maximum of the cardiac function, and possibly a local maximum of the cardiac function. If the above described method is aborted after a specific criteria is satisfied, the best performing point (i.e., the set of pacing parameters producing the best cardiac performance value) can be selected and used for further pacing of the heart.

BRIEF DESCRIPTION OF THE DRAWINGS/FIGURES

Further features and advantages of the present invention may be more readily understood by reference to the following description taken in conjunction with the accompanying drawings, in which:

FIG. 7 is a flow chart useful for describing an overview of the operation of an embodiment of the present invention.

DETAILED DESCRIPTION OF THE INVENTION

Figure 1:
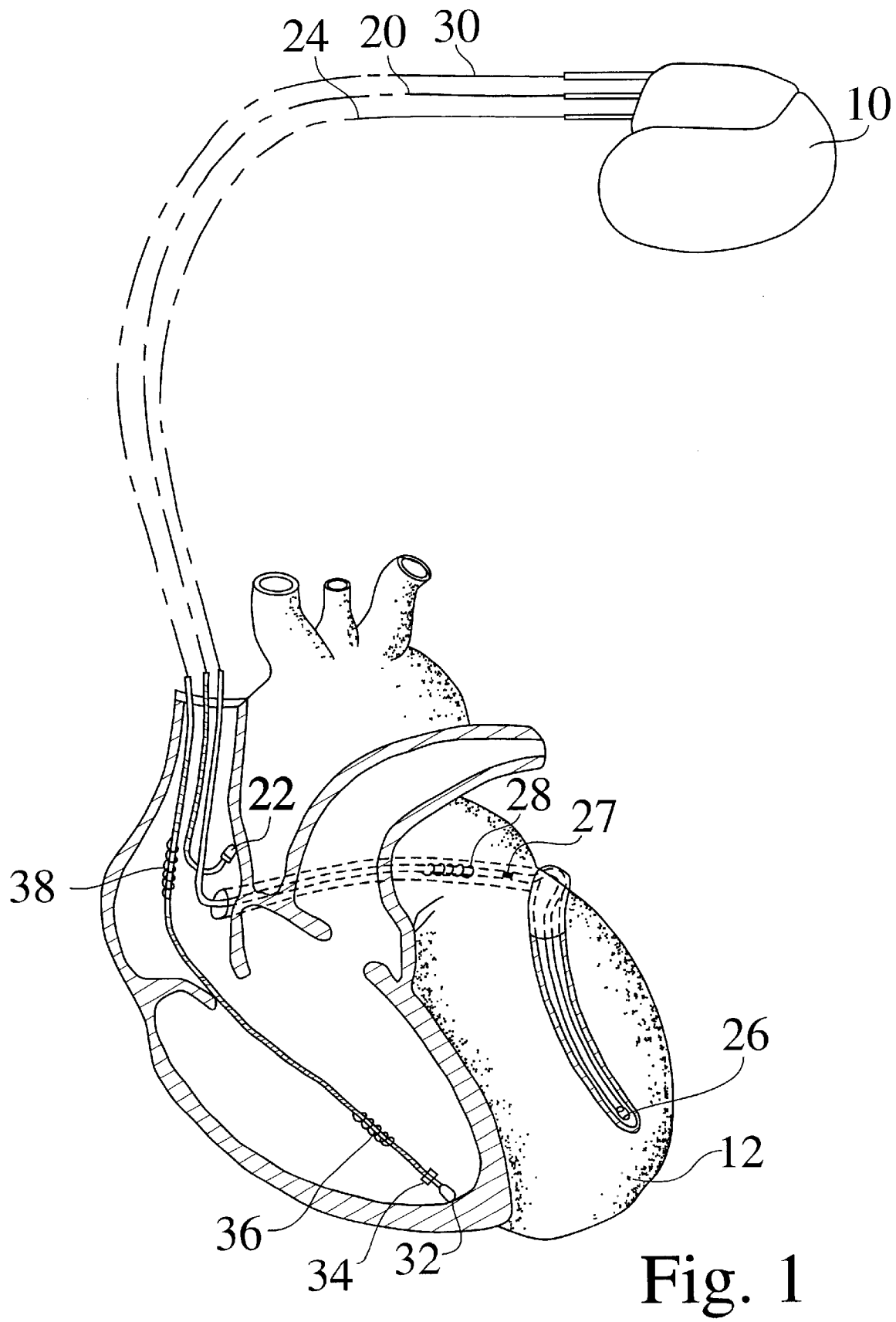
FIG. 1 is a simplified diagram illustrating an implantable stimulation device in electrical communication with at least three leads implanted into a patient's heart for delivering multi-chamber stimulation and shock therapy.

The following description is of the best modes presently contemplated for practicing the invention. This description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout.
Exemplary Stimulation Device As shown in FIG. 1, there is an exemplary stimulation device 10 (also referred to as a pacing device, or a pacing apparatus) in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

Figure 2:
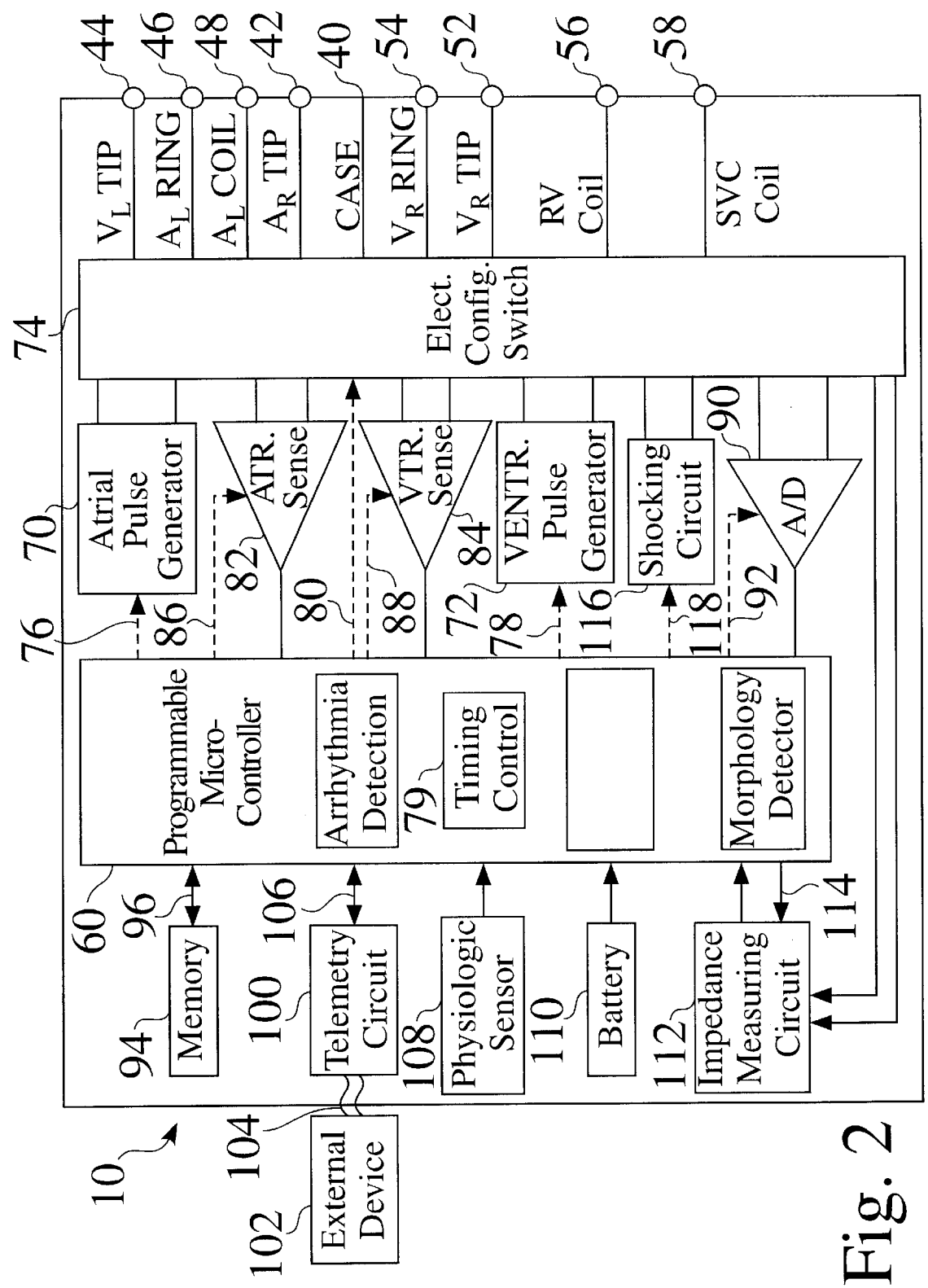
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively. At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design of the microcontroller 60 are not critical to the present invention. Rather, any suitable microcontroller 60 can be used to carry out the functions described herein. The use of microprocessor-based control circuits for performing timing and data analysis functions are well known in the art. In specific embodiment of the present invention, the microcontroller 60 performs some or all of the steps associated with determining optimal pacing parameters in accordance with the present invention.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the stimulation device and their inter-relationship, see U.S. Pat. No. 4,788,980 (Mann et. al.). The '052, '555, '298 and '980 patents are incorporated herein by reference.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control pacing parameters (e.g., the timing of stimulation pulses) as well as to keep track of the timing of refractory periods, PVARP intervals, noise detection windows, evoked response windows, alert intervals, marker channel timing, etc., which is well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

The switch bank 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. Such sensing circuits, 82 and 84, can be used to determine cardiac performance values used in the present invention.

The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity, in the appropriate chambers of the heart. The sensing circuits, 82 and 84, in turn, receive control signals over signal lines, 86 and 88, from the microcontroller 60 for purposes of measuring cardiac performance at appropriate times, and for controlling the gain, threshold, polarization charge removal circuitry (not shown), and timing of any blocking circuitry (not shown) coupled to the inputs of the sensing circuits, 82 and 86.

For arrhythmia detection, the device 10 utilizes the atrial and ventricular sensing circuits, 82 and 84, to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 can be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

A feature of the present invention is the ability to sense and store a relatively large amount of data (e.g., from the data acquisition system 90). Such data can then be used for subsequent analysis to guide the programming of the device and/or to appropriately adjust pacing parameters in accordance with embodiments of the present invention.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to an external device 102 through an established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. patent application Ser. No. 09/223,422, filed Dec. 30, 1998, entitled "Efficient Generation of Sensing Signals in an Implantable Medical Device such as a Pacemaker or ICD" (note: this relates to transfer of EGM data) (McClure et al.), which patents are hereby incorporated herein by reference.

In the preferred embodiment, the stimulation device 10 further includes a physiologic sensor 108, that can be used to detect changes in cardiac performance or changes in the physiological condition of the heart. Accordingly, the microcontroller 60 can respond by adjusting the various pacing parameters (such as rate, AV Delay, RV-LV Delay, V-V Delay, etc.) in accordance with the embodiments of the present invention. The microcontroller 60 controls adjustments of pacing parameters by, for example, controlling the stimulation pulses generated by the atrial and ventricular pulse generators, 70 and 72. While shown as being included within the stimulation device 10, it is to be understood that the physiologic sensor 108 may also be external to the stimulation device 10, yet still be implanted within or carried by the patient. More specifically, the sensor 108 can be located inside the device 10, on the surface of the device 10, in a header of the device 10, or on a lead (which can be placed inside or outside the bloodstream).

The stimulation device 10 additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 10 must also have a predictable discharge characteristic so that elective replacement time can be detected. Accordingly, the device 10 preferably employs lithium/silver vanadium oxide batteries, as is true for most (if not all) current devices.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 via a control signal 114. The known uses for an impedance measuring circuit 120 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used. The impedance measuring circuit 112 is not critical to the present invention and is shown only for completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too dis-organized to be recognize), and pertaining exclusively to the treatment of fibrillation. Accordingly, the microcontroller 60 is capable of controlling the synchronous or asynchronous delivery of the shocking pulses.

Operation of the Present Invention

Figure 3:
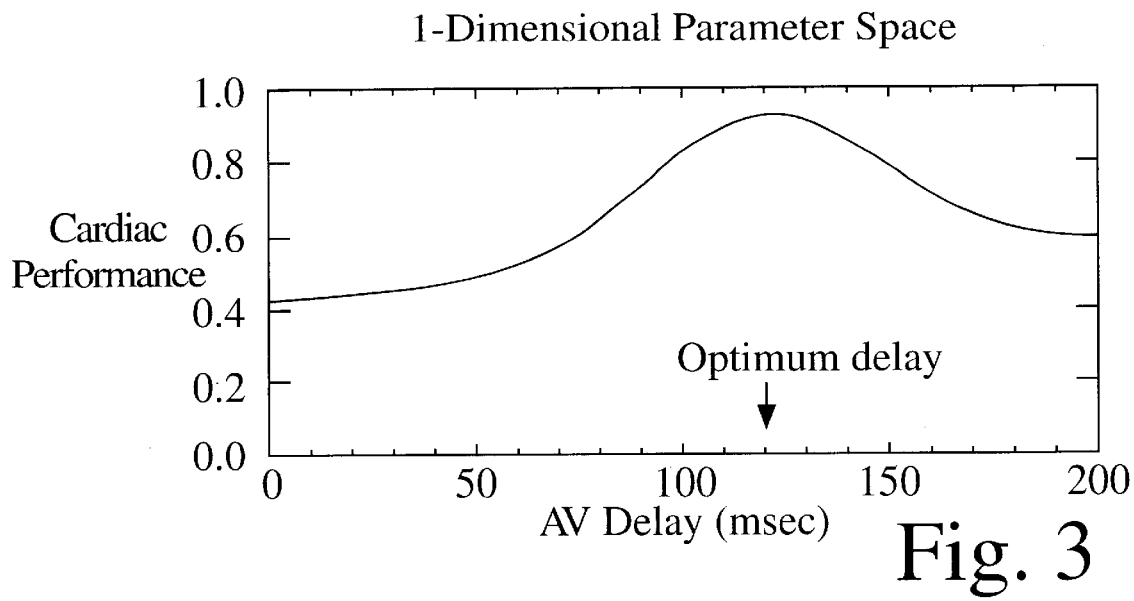
FIG. 3 is graph of a one-dimensional parameter space that illustrates cardiac performance as a function of AV delay.

As discussed above, there is a need for efficient and effective methods, systems and devices for optimizing multiple pacing parameters. This is because the number of potential pacing parameter combinations increases dramatically as the number of sites paced increases, making it potentially difficult and time consuming to determine optimal pacing parameters. This problem can be formulated in terms of an abstract mathematical space, where each dimension of the space represents an adjustable independent pacing parameter. For example, in dual-chamber pacing (e.g., right atrium and right ventricle pacing) there is a single independent parameter, the atrioventricular (AV) delay, and cardiac performance is a function of this one parameter. An example of such a one-dimensional parameter space is shown in FIG. 3. In FIG. 3, each point in the space is associated with a cardiac performance (as defined by the y-axis) that results when a heart is paced such that it has a specific AV delay (as defined by the x-axis).

Figure 4:
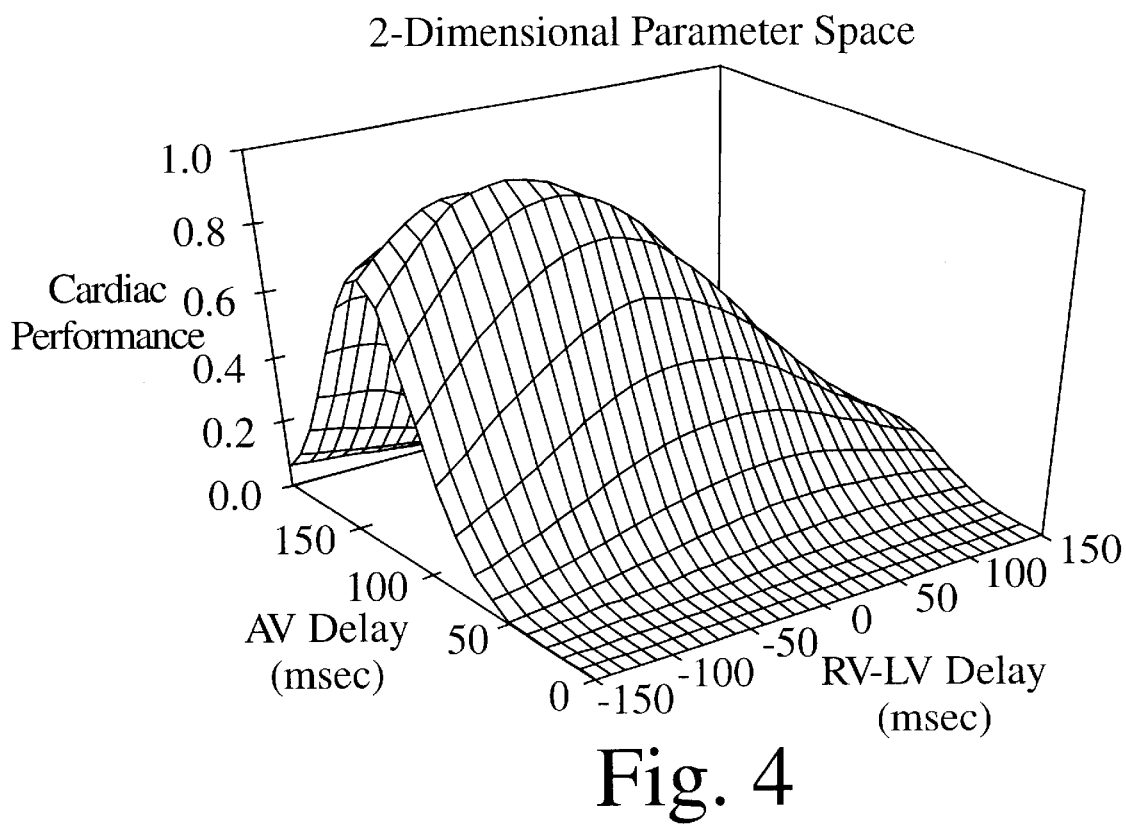
FIG. 4 is a graph of a two-dimensional parameter space that illustrates cardiac performance as a function of AV delay and RV-LV delay.

In three chamber pacing (e.g., right atrium, right ventricle and left ventricle) there are two independent parameters (AV delay and interventricular RV-LV delay), and thus, a two dimensional parameter space, with each point in the space representing a particular parameter pair. Associated with each point in space is also the cardiac performance that results from that parameter pair setting. A corresponding two-dimensional parameter space resembles a mountainous landscape that forms a three-dimensional surface over a two-dimensional latitude/longitude grid, as shown in FIG. 4. In FIG. 4, each point in the space is associated with a cardiac performance (as defined by the z-axis) that results when the heart is paced such that it has a specific AV delay (as defined by the y-axis) and a specific RV-LV delay (as defined by the x-axis). Parameter optimization in this case consists of finding the coordinates of the peak of the mountainous landscape, which represents the peak in cardiac performance.

The above discussed problem can be generalized to any number of dimensions. For example, the parameter space of a four-chamber pacemaker would have three dimensions. Similarly, pacing rate could be treated as a parameter to be optimized, which would add an additional dimension to the space.

As discussed above, an exhaustive search of parameter space becomes unworkable as the number of pacing parameters, and thus, dimensions, increases. The present invention enables efficient and effective determinations of optimum pacing parameters when multiple sites are being paced. The present invention can also be used when only one site is being paced (e.g., if only AV delay is being optimized).

If the problem of determining optimal pacing parameters is formulated in terms of an abstract mathematical space, where each dimension of the space represents an adjustable independent pacing parameter, then the solution is finding the point in the abstract mathematical space having the maximum cardiac performance value. For example, if the problem is to find the optimal pacing parameters in dual-chamber pacing, then the solution is to find the AV delay that provides the maximum cardiac performance. Referring to the one-dimensional parameter space shown in FIG. 3, the maximum cardiac function occurs when the AV delay is 120 msec. For another example, if the problem is to find the optimal pacing parameters in three-chamber pacing, then the solution is to find the AV delay and the RV-LV delay associated with the peak of the mountainous landscape shown in FIG. 4.

One solution for determining optimum pacing parameters (e.g., a set of pacing parameters associated with the peak of the mountainous landscape shown in FIG. 4) is to move a single point successively through the space in a way that optimizes the cardiac performance. When applied to an automatic optimization algorithm, the algorithm would use feedback from a physiologic sensor(s) to assess the effectiveness of a particular set of pacing parameters.

In contrast to algorithms that move a single point throughout parameter space, the present invention applies evolutionary algorithms that maintain a population of points (i.e., a plurality of sets of pacing parameters). This can be explained by way of an example discussed with reference to FIGS. 5A, 5B and 5C, which are useful for showing how the two-dimensional parameter space (e.g., the parameter space of FIG. 4) can be efficiently and effectively searched using the evolutionary approach of the present invention. When applied to an automatic optimization algorithm, the present invention uses feedback from a physiologic sensor(s) to assess the effectiveness of multiple sets of pacing parameters.

Figure 5A:
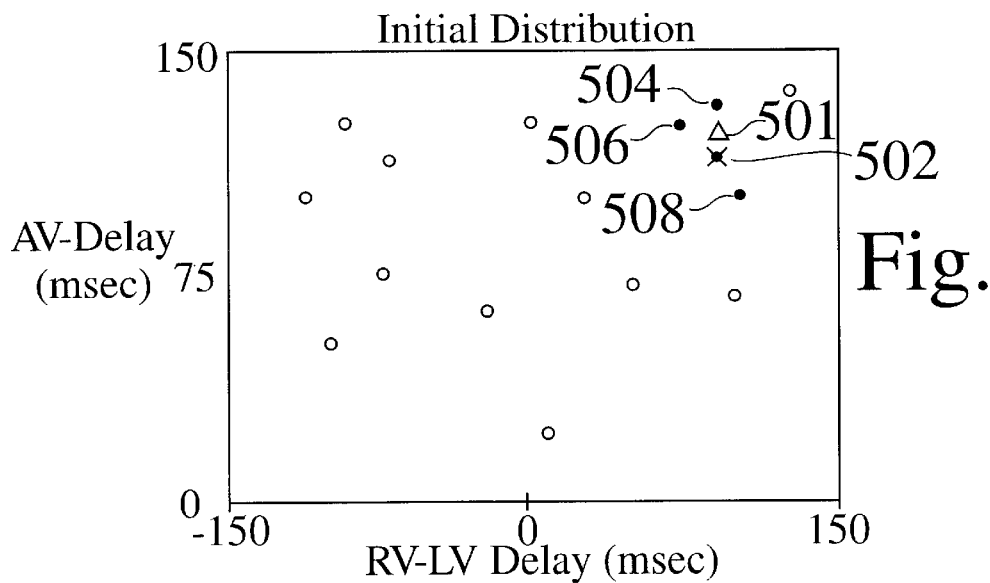
FIGS. 5A, 5B and 5C show points within a two-dimensional parameters space defined by AV delay and RV-LV delay, which are useful for describing an embodiment of the present invention.

FIG. 5A shows an initial population of M=16 points, where each point represents a set of N=2 pacing parameters (i.e., AV delay and RV-LV delay). A triangle ($\Delta$) 501 represents the location in the parameter space of the global maximum of a heart's cardiac function. For example,: if a mountainous landscape over an AV/RL-LV grid is used to show a heart's cardiac function (e.g., as in FIG. 4), the global maximum is the location of the peak of the mountainous landscape.

Multisite pacing pulses are delivered to the heart according to the delays defined by each point in the population. For each point, a hemodynamic variable (also referred to as a cardiac performance value) or surrogate is measured and stored.

An updated population of points is then created based on the performance of the members of the current population of points. For example, an updated population of points is based on one or more of the best performing points (i.e., based on one or more of the sets of pacing parameters resulting in the best cardiac performance) of the current population of points. In one embodiment, the best performing 25% of the points (i.e., the sets of pacing parameters corresponding to the best 25% of cardiac performance values) are selected. Referring to FIG. 5A, points 502, 504, 506 and 508 (each represented by a "•") are the best performing points, with point 502 (shown with an "x") being the best performing point. Each of the remaining points (i.e., those points represented by a "○") is replaced with a randomized version of one of the best performing points (i.e., one of points 502, 504, 506 or 508). In this example, the updated population of points, shown in FIG. 5B, includes the best performing points (i.e., points 502, 504, 506 and 508) and randomized versions of the best performing points which have replaced the worst performing points. Various alternative ways of creating an updated population of points are discussed in more detail below.

Figure 5B:
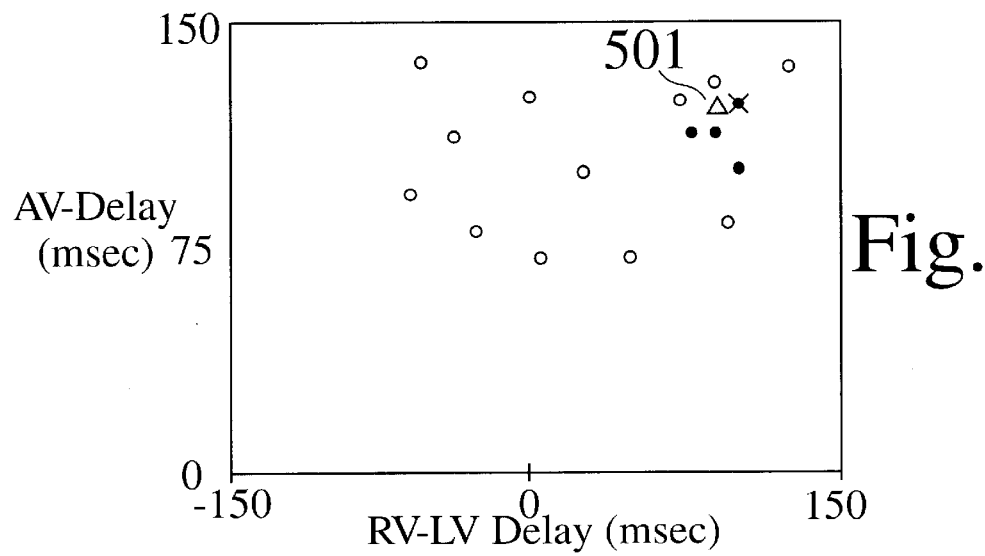

Multisite pacing pulses are then delivered to the heart according to the delays defined by each point in the updated population, shown in FIG. 5B. For each point a hemodynamic variable (also referred to as cardiac performance value) or surrogate is measured. As shown, a point that was one of 25% best points in the original population of points shown in FIG. 5A, may not be one of the 25% best performing points in the new updated population of points shown in FIG. 5B.

Figure 5C:
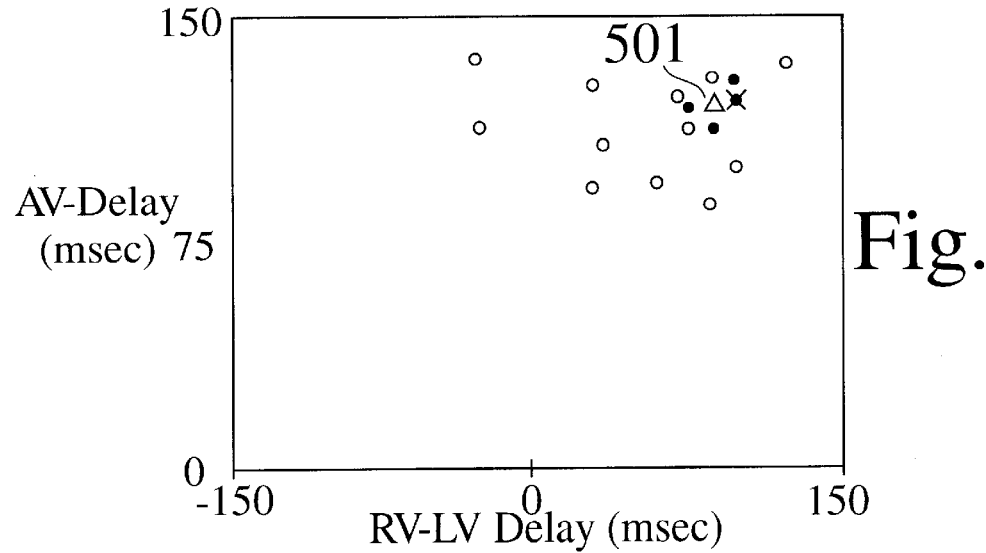

A new updated population of points is then created based on one or more of the best performing points of the previous updated population of points (e.g., based on the 25% best points), in a manner similar to that described above. For example, a new updated population of points is shown in FIG. 5C. It is noted that the best performing point can change, as shown, since one of the new points in the new updated population of points can produce better cardiac performance than the previous best performing point.

In a steady state, the location 501 of the global maximum of the cardiac function typically does not change, and the population tends to cluster around that location 501. This is induced by the selection process. This is also balanced by the tendency to diverge away from the location 501 of the global maximum, which is induced by the randomization process. As the location 501 of the global maximum shifts, for example, due to a change in posture, the population of points will track its trajectory.

The above described method can be repeated indefinitely, or until a specific criterion is satisfied. During performance of the above described method the heart will be paced according to a plurality of different sets of pacing parameters each of which should eventually be close to the location of global maximum for a corresponding physiologic condition (e.g., subject resting, subject undergoing physical excersion, etc.). If the above described method is aborted after a specific criterion is satisfied, the best performing point (i.e., the set of pacing parameters producing the best cardiac performance value) of the latest plurality of points can be selected and used for further pacing of the heart.

Figure 6A:
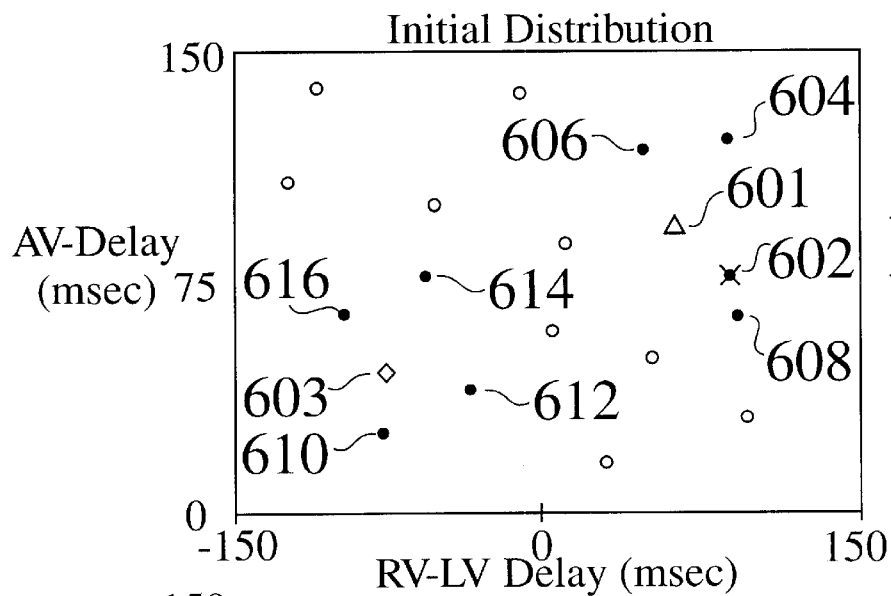
FIGS. 6A, 6B and 6C show points within a two-dimensional parameters space defined by AV delay and RV-LV delay, which are useful for describing an embodiment of the present invention where both global and local maxima of a cardiac function are tracked.
Figure 6B:
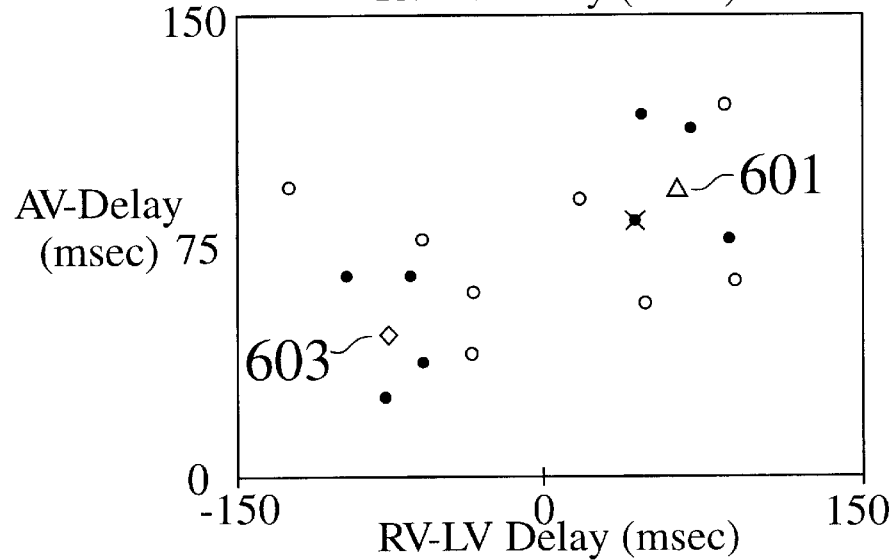
Figure 6C:
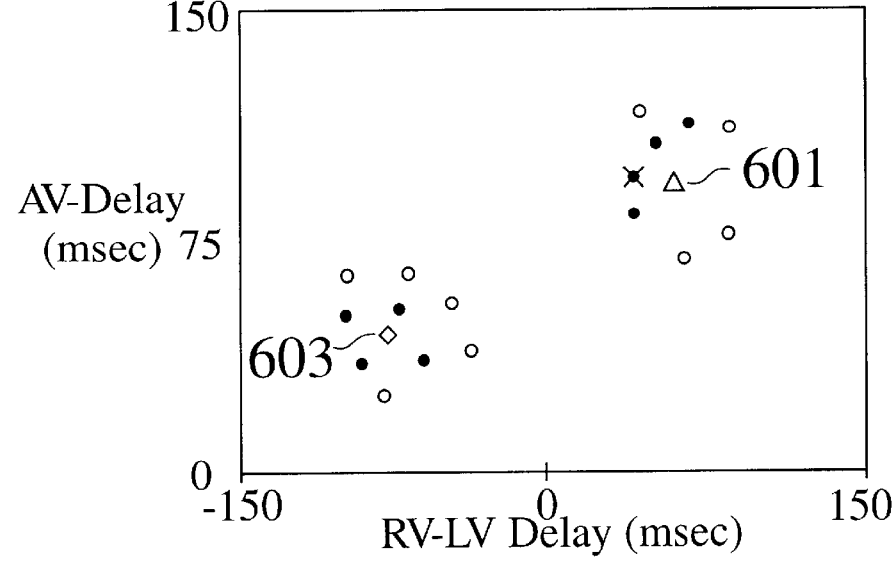

FIGS. 6A, 6B and 6C are useful for showing how the location of both global and local maxima of a cardiac function can be tracked using the present invention. This is important where the cardiac function of a patient is such that more than one area within a parameter space provides good cardiac performance. In terms of a two-dimensional parameter space, such a patient's cardiac function would resemble a mountainous landscape (that forms a three-dimensional surface over a two-dimensional latitude/longitude grid) having more than one peak (e.g., a mountainous landscape similar to that shown in FIG. 4, but having two peaks, one most likely being higher than the other).

FIG. 6A shows of population of M=16 points, where each point represents a set of N=2 pacing parameters (i.e., AV delay and RV-LV delay). A triangle ($\Delta$) 601 represents the location in the parameter space of the global maximum of a heart's cardiac function. A diamond ($\Diamond$) 603 represents the location of a local maximum of the heart's cardiac function.

Multisite pacing pulses are delivered to a heart according to the delays defined by each point in the population. For each point, a hemodynamic variable (also referred to as cardiac performance value) or surrogate is measured and stored.

An updated population of points is then created based on one or more of the best performing points (i.e., based on one or more of the sets of pacing parameters resulting in the best cardiac performance). In this example, an average cardiac performance value is determined. Then, those points (i.e., sets of pacing parameters) corresponding to cardiac performance values less than the average cardiac performance value are removed and replaced with randomized versions of those points (i.e., sets of pacing parameters) corresponding to cardiac performance values greater than the average. Referring to FIG. 6A, points 602, 604, 606, 608, 610, 612,

614 and 616 (each represented by a "•") correspond to cardiac performance values greater than the average, with point 602 (shown with an "×") being the best point.

Each of the remaining points (each represented by a "○") is replaced with a randomized version of one of the best performing points (i.e., a randomized version of one of points 602, 604, 606, 608, 610, 612, 614 or 616). In this example, the updated population of points, shown in FIG. 6B, includes the best performing points (i.e., points 602, 604, 606, 608, 610, 612, 614 and 616) and randomized versions of the best performing points that have replaced the worst performing points. Various alternative ways of creating an updated population of points are discussed in more detail below. Multisite pacing pulses are then delivered to the heart according to the delays defined by each point in the updated population. For each point a cardiac performance value or surrogate is measured.

An updated population of points is then created based those points associated with cardiac performance values greater than an updated average cardiac performance value, in a manner similar to that described above. The new updated population of points is shown in FIG. 6C. It is noted that the best point can change since some of the new points in the updated population of points can produce better cardiac performance than the previous best point.

In a steady state, the population of points tends to cluster around the locations of the global and local maxima of the cardiac function (i.e., around locations 501 and 503). This is induced by the selection process. This is also balanced by the tendency to diverge away from the maxima, which is induced by the randomization process. As the location of the global and local maxima shift, for example, due to a change in posture, the populations will track their trajectory. It is also possible that when a patient's cardiac function changes (e.g., as when a patient moves from supine to walking), the cardiac function landscape shifts such that what was once a lower peak becomes a dominant peak. This can cause a point in the cluster near what used to be the local maximum to become the best performing point. For example, referring to FIG. 6C, when the patient goes from being inactive to active, the global maximum may change from being a location about which the top right cluster of points converge, to being a location about which the lower left cluster of points converge.

The present invention shall now be described in additional detail in connection with FIG. 7 and the remaining figures. In FIG. 7, a flow chart is shown describing an overview of the operation and features implemented in an embodiment of the device 10. Alternatively, these features can be performed by an external device (e.g., external device 102) that communicate with the device 10. The external device 102 together and in communication with device 10 form a system. Such features can be used to efficiently and effectively determine sets of optimum or substantially optimum pacing parameters. In this flow chart and the other flow charts described herein, the various algorithmic steps are summarized in individual "blocks". Such blocks describe specific actions or decisions to be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art can readily write such a control program based on the flow charts and other descriptions presented herein. The steps of a flowchart are collectively referred to as a method. For example, the steps in the flowchart of FIG. 7 shall be referred to as a method 700 of the present invention.

Method 700 of the present invention shall now be described with reference to FIG. 7. Method 700 starts at step 701 and proceeds immediately to step 702. At step 702, an initial plurality of sets (i.e., M sets) of pacing parameters are determined, wherein each set of pacing parameters includes N pacing parameters that are being optimized. That is, at step 702, M sets of N pacing parameters are initialized, where N represents the number of pacing parameters being optimized and M represent the number of different sets. For example, in a dual-chamber pacing embodiment, only one pacing parameter is being optimized (e.g., AV delay), and thus, N=1. In a three-chamber pacing embodiment, two pacing parameters are being optimized (e.g., AV delay and RV-LV delay), and thus, N=2. If four pacing parameters are being optimized, then N=3, and so on. It is noted that pacing rate is another example of a type of pacing parameter. Assuming that both AV delay and RV-LV delay are being optimized (and thus, that N=2), an example of one of the initial sets of pacing parameters, of the plurality of sets of pacing parameters, is {AV delay=150 msec; RV-LV delay= 20 msec}.

In a preferred embodiment, the initial M sets of pacing parameters (i.e., M points) are selected at random. Any known algorithm for selecting a random or approximately random M sets can be employed. In another embodiment, the initial M sets of pacing parameters are selected such that a uniform coverage of the applicable parameter space is selected. In still another embodiment, the initial M sets of pacing parameters are predefined (e.g., predetermined based on an educated guess). In a further embodiment, the initial M sets of pacing parameters can be selected from X sets of pacing parameters, where X>M.

At a next step 704, cardiac performance associated with each of the plurality of sets (e.g., M sets) of N pacing parameters is determined. This can be accomplished by measuring cardiac performance when the heart is paced using each of the plurality of sets (e.g., each of the M sets) of N pacing parameters, thereby determining a corresponding plurality of cardiac performance values (e.g., M values). Measurements of cardiac performance are also referred to as pulse amplitude measurements, hemodynamic response measurements, cardiac function measurements, or surrogate measurements.

The pulse amplitude can be obtained in a variety of ways. For example, in one embodiment pulse amplitude (i.e., cardiac performance or hemodynamic response) is a measure of ventricular pressure, or the time-derivative of ventricular pressure, as determined by an intracavitary pressure transducer. In an alternative embodiment, vascular plethysmography is used to obtain a measure of arterial pulse amplitude. In another embodiment, heart sounds are used to obtain a measure of the strength of cardiac contraction. Other measures of cardiac performance are possible, including ultrasound to detect changes in the diameter of the aorta or other vessels during the cardiac cycle, Doppler ultrasound to detect the blood flow through arteries, cardiac motion detected by an accelerometer, ventricular volume detected by intracardiac or extracardiac impedance plethysmography. Still another measure of cardiac function is mechanical distension of arteries, which can be measured, for example, using a strain gauge, an accelerometer, or a pressure transducer. Thus, the term 'pulse amplitude' is intended to be used in the generic sense as some measure of cardiac performance. Such measures of cardiac performance can be generated, for example, on a beat-by-beat basis. Arterial pulse amplitudes, which are pulse amplitude measures derived from an increased pressure and distension of the arterial vasculature that results from a systolic pulse, may alternatively be used. Measures of arterial pulse amplitude include, for example, optical vascular plethysmography, intra- or extra-arterial pressure transduction, and ultrasound sensing. In one embodiment, step 704 can be broken into more detailed steps 802 through 824 of FIG. 8A, which are discussed below.

At a next step 706, a least one set of pacing parameters is selected from the M sets of N pacing parameters, based on the cardiac performance values determined at step 704. This can be accomplished in a variety of different ways, as will be discussed below.

At a step 708, an updated plurality of sets of pacing parameters is created based on the at least one set of pacing parameters selected at step 706. This step also can be accomplished in a variety of different ways, as will be discussed below.

Steps 704, 706 and 708 are repeated a plurality of times, wherein each time steps 704 and 706 are repeated, the updated plurality of sets of pacing parameters created during the most recent performance of step 708 are used. During performance of method 700, the heart will be paced according to a plurality of different sets of pacing parameters that should all eventually evolve toward and be close to an optimum set of pacing parameters (or optimal sets of pacing parameters, depending on the embodiment).

Steps 704, 706 and 708 can be repeated indefinitely. This would allow method 700 to be responsive to rapid changes in hemodynamics, as when a patient moves from supine to walking. Additionally, such a method enables continual on-the-fly pacing optimization. Further, this method for optimizing pacing parameters allows the pacing parameters to track slowly changing hemodynamic variables, such as heart rate, autonomic tone, or blood pressure, as well is disease progression.

Steps 704, 706 and 708 of method 700 need not continue indefinity. In an alternative embodiment, the present invention is used to determine pacing parameters that will be programmed (e.g., permanently) into a pacing device. In such an embodiment, steps 704, 706 and 708 can be repeated a predetermined number of times (e.g., the method is repeated until each of the steps is performed 10 times).

In other embodiments, steps 704, 706 and 708 can be repeated until a specific criteria is satisfied. For example, an average cardiac performance value can be determined each time step 704 is performed (e.g., this can be accomplished by adding M cardiac performance values determined at step 704, and then dividing the total sum by M). In one embodiment, steps 704, 706 and 708 can be repeated until the difference between two consecutive determined average cardiac performance values is less than a predetermined value. In another embodiment, steps 704, 706 and 708 can be repeated until a variance between the cardiac performance values (determined at step 704) is less than a predetermined value. Each of these embodiments would provide confidence that the plurality of sets of pacing parameters have settled close to an optimal point in parameter space. The set of pacing parameters producing the best cardiac performance value can be selected (from the most recently created plurality of sets of pacing parameters) and used for further pacing of the heart.

In some embodiments, the updated plurality of sets of pacing parameters produced at step 708 includes the same amount of sets (or approximately the same amount of sets) as the previous plurality of sets of pacing parameters. For example, if M sets of pacing parameters were determined at step 702, then M updated sets of pacing parameters are created at step 708. In alternative embodiments, each time the updated sets of pacing parameters are created, the updated plurality of sets of pacing parameters includes less sets than the previous plurality of sets of pacing parameters. In these alternative embodiments, eventually only one set of pacing parameters remains, wherein the remaining set is used for further pacing of the heart.

Various ways of practicing steps 706 and 708 shall now be discussed. In one embodiment, step 706 includes selecting a predetermined percentage of the plurality of sets of parameters based on the cardiac performance values determined at step 704. For example, step 706 can include selecting the sets of pacing parameters corresponding to the best 50% (or some other percentage) of the cardiac performance values determined at step 704.

In another embodiment, step 706 includes selecting the set of pacing parameters associated with a maximum cardiac performance value determined at step 704 (this set is referred to as the best set) and selecting each set of pacing parameters within a predetermined range of the best set. For example, referring back to FIG. 5A, point 502 (represented by an "×") represents the best set of pacing parameters (i.e., the set of pacing parameters producing the highest cardiac performance value) and points 506, 508 and 510 represent those sets of pacing parameters that are within a specific region 504 of parameter space about point 502.

In still another embodiment, step 706 includes determining an average cardiac performance value (based on the cardiac performance values determined at step 704) and selecting the sets of pacing parameters corresponding to cardiac performance values that are greater than the average cardiac performance value.

In yet another embodiment, step 706 includes assigning probabilities to the each of the sets of pacing parameters based on the cardiac performance values determined at step 704. These assigned probabilities determine the probability that a set will be selected (and thus, the probability of whether a set's attributes are passed to the succeeding generation). The sets (i.e. points) with better performance values are assigned higher probabilities than those with worse performance values. For example, the sets of pacing parameters can be ranked according to their performance values, and assigned the probability $p=1-(r-1)/(M-1)$, where p is the probability assigned to each set, r is the rank of a set from 1 to M, and M is the number of sets (i.e., points) in the population. Thus, in this example, the best performing set of pacing parameters would receive the probability 1, the worst performing set of pacing parameters would receive the probability 0, and the rest of the population would receive a probability proportional to their rank. Other probability assignments are of course possible. Once the probabilities have been assigned, sets of pacing parameters are selected based on the probabilities assigned to the sets. Note that assigning a probability of 1 to those sets with performance better than the average, and a probability 0 to those sets with performance worse than the average, is mathematically equivalent to the selection technique described in the preceding paragraph.

These are only a few examples of how at least one set of pacing parameters can be selected (at step 706) from the plurality of sets of pacing parameters based on the cardiac performance values determined at step 704. Various other ways of selecting the at least one set of pacing parameters will be apparent to a person skilled in the relevant art and are within the spirit and scope of the present invention.

Now referring again to step 708, the updated plurality of sets of pacing parameters created at step 708 can include one or more of the same sets of pacing parameters used to pace the heart at step 704, one or more new sets of pacing parameters, or a combination thereof.

In one embodiment, step 708 includes replacing each set of pacing parameters selected at step 706 with one, two (or more) randomized versions (also referred to as daughters) of the set. A randomized version of a set of pacing parameters can be created in various ways, as will be explained in more detail below. The updated plurality of sets of pacing parameters includes the created randomized versions. For example, in one embodiment the worst performing 50% of the sets of pacing parameters are removed, and each of the remaining sets of pacing parameters is replaced by two daughter sets.

In another embodiment, step 708 includes replacing the sets of pacing parameters not selected at step 706 with randomized versions of the sets of pacing parameters selected at step 706. The updated plurality of sets of pacing parameters can include only the created randomized versions. Alternatively, the updated plurality of sets of pacing parameters can also include those sets of pacing parameters selected at step 706 (e.g., the best performing 50% of the sets of pacing parameters). For example, in one embodiment the worst performing 50% of the sets of pacing parameters are replaced by randomized versions of the best performing 50% of the sets of pacing parameters. The updated plurality of sets of pacing parameters can include only the randomized versions (i.e., only the daughter sets). Alternatively, the updated plurality of sets of pacing parameters can include the daughter sets and the best performing 50% of the sets of pacing parameters (also referred to as parent or mother sets).

These are only a few examples of how the updated plurality of sets of pacing parameters can be created at step 708. Various other ways of creating the updated plurality of sets of pacing parameters will be apparent to a person skilled in the relevant art and are within the spirit and scope of the present invention.

It is noted that steps 706 and 708 are not necessarily performed one after another, but rather, can be performed somewhat simultaneously. For example, each time a set of pacing parameters is selected or removed, it can be immediately replaced with a randomized version of that set, or a randomized version of another one of the plurality of sets of pacing parameters. It is also noted that the term "selecting" in this invention can refer to "not being removed, replaced or rejected." In other words, the at least one set of pacing parameters selected at step 706 can be one or more sets of pacing parameters that are not removed or replaced.

Various ways of producing a randomized version of a set of pacing parameters (also referred to as a daughter point or daughter set) shall now be discussed.

For example, in an embodiment where each of the best performing sets of pacing parameters is replaced with a daughter set, each daughter can inherit pacing parameters of its parent set (e.g., one of the best performing sets), to which is added a zero mean, 10 msec standard deviation, gaussian random variable. This will cause the daughter sets to be modestly and randomly displaced copies of the parents. Similarly, in an embodiment where each of the worst performing sets of pacing parameters is replaced with a daughter of one of the best performing sets of pacing parameters, each daughter can inherit pacing parameters of one of the best performing sets, to which is added a zero mean, 10 msec standard deviation, gaussian random variable. Of course, other means, standard deviations, and probability density functions can be used.

In an embodiment of the present invention, daughter sets are generated by simply adding random increment values to a parent set, wherein the random increment values are selected from a predetermined group of increment values. In one embodiment, the range from which random values are selected is shrunk (i.e., made smaller) each time the updated plurality of sets of pacing parameters are produced at step 708. This can help accelerate finding optimum sets of pacing parameters. For example, the maximum possible increment value can be 30 msec the first time step 708 occurs; 25 msec the second time step 708 occurs; 20 msec the third time step 708 occurs, and so on.

In another embodiment, each pacing parameter is coded with a number of 'genes', which are summed together to provide a pacing parameter. The genes are randomly altered and exchanged among selected sets of pacing parameters in a way analogous to sexual reproduction. In still another embodiment, genes are randomly altered and directly passed to daughter points without exchange with other survivors in a way analogous to asexual reproduction.

For example, assume a first set of pacing parameters selected at step 706 is {AV delay=180 msec, with genes 50, 55, 75, where 50+55+75=180; RV-LV delay=50 msec, with genes 14, 16 and 20, where 14+16+20=50}. Also assume that a second set of pacing parameters is {AV delay=160 msec, with genes 40, 42, 78, where 40+42+78=160; RV-LV delay=70 msec, with genes 22, 23 and 25, where 22+23+25=70}. The genes of each set can be randomly altered and exchanged in a way analogous to sexual reproduction. For example, random increment values can be added to each of genes 50, 55 and 75 of the first set, and random increment values can be added to each of genes 40, 42 and 78 of the second set. Then one or more of the randomly altered genes associated with the first set can be traded for one or more of the randomly altered genes associated with the second set. The genes can then be added together to create AV delays of daughter sets. The RV-LV delays of daughter sets can be created in a similar manner.

Alternatively, the each sets' genes can be randomly altered and directly passed to a new set (i.e., a daughter point), without exchange with the another set, in a way analogous to asexual reproduction. For example, random increment values can be added to each of genes 50, 55 and 75 of the first set. Then the randomly altered genes can be added together (without any trading with another set) to create the AV delay of a daughter of the first set. The RV-LV delay of a daughter of the first set can be created in a similar manner.

Figure 8A:
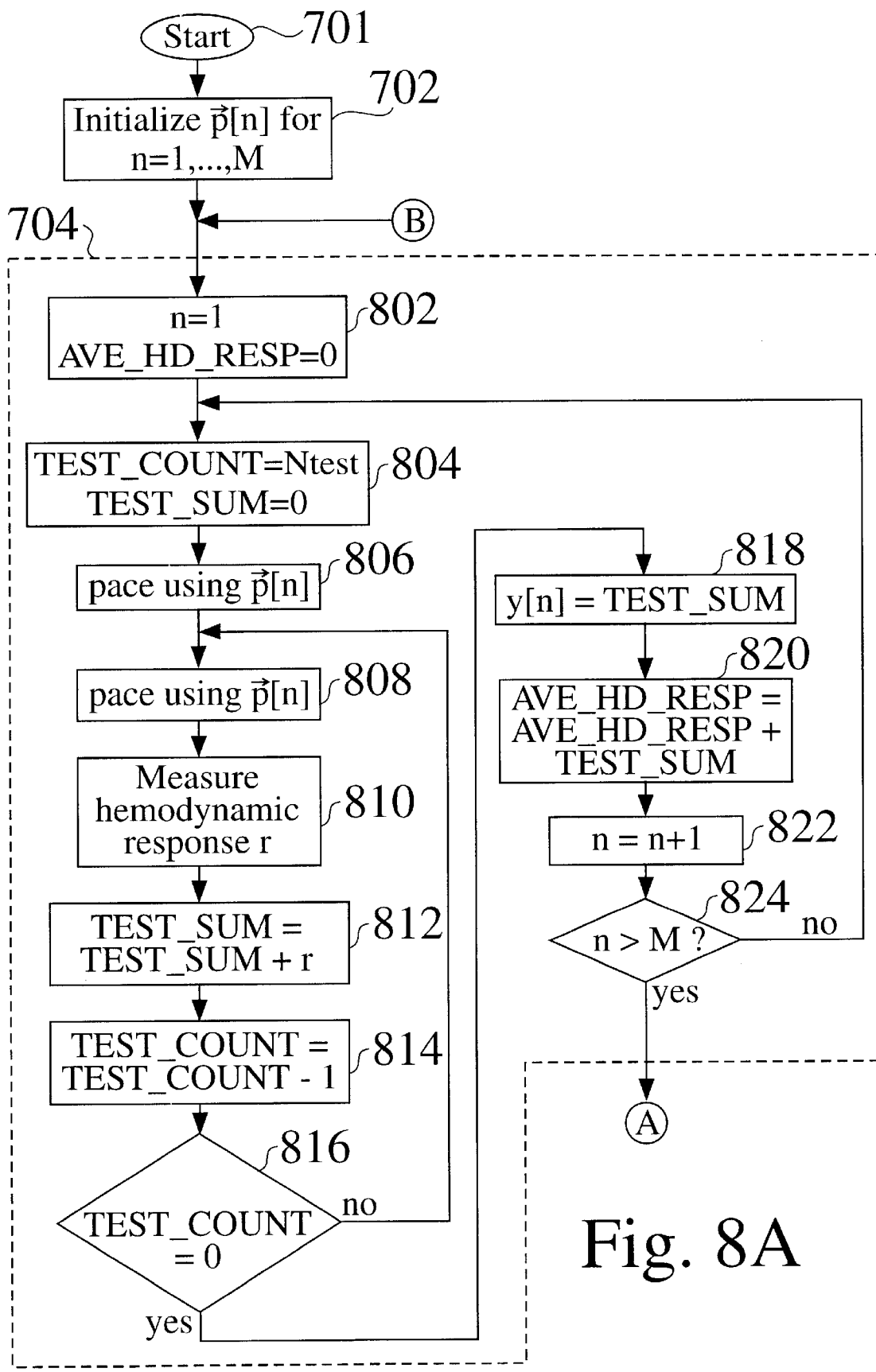
FIGS. 8A and 8B together illustrate a flow chart useful for describing operation of a specific embodiment of the present invention.
Figure 8B:
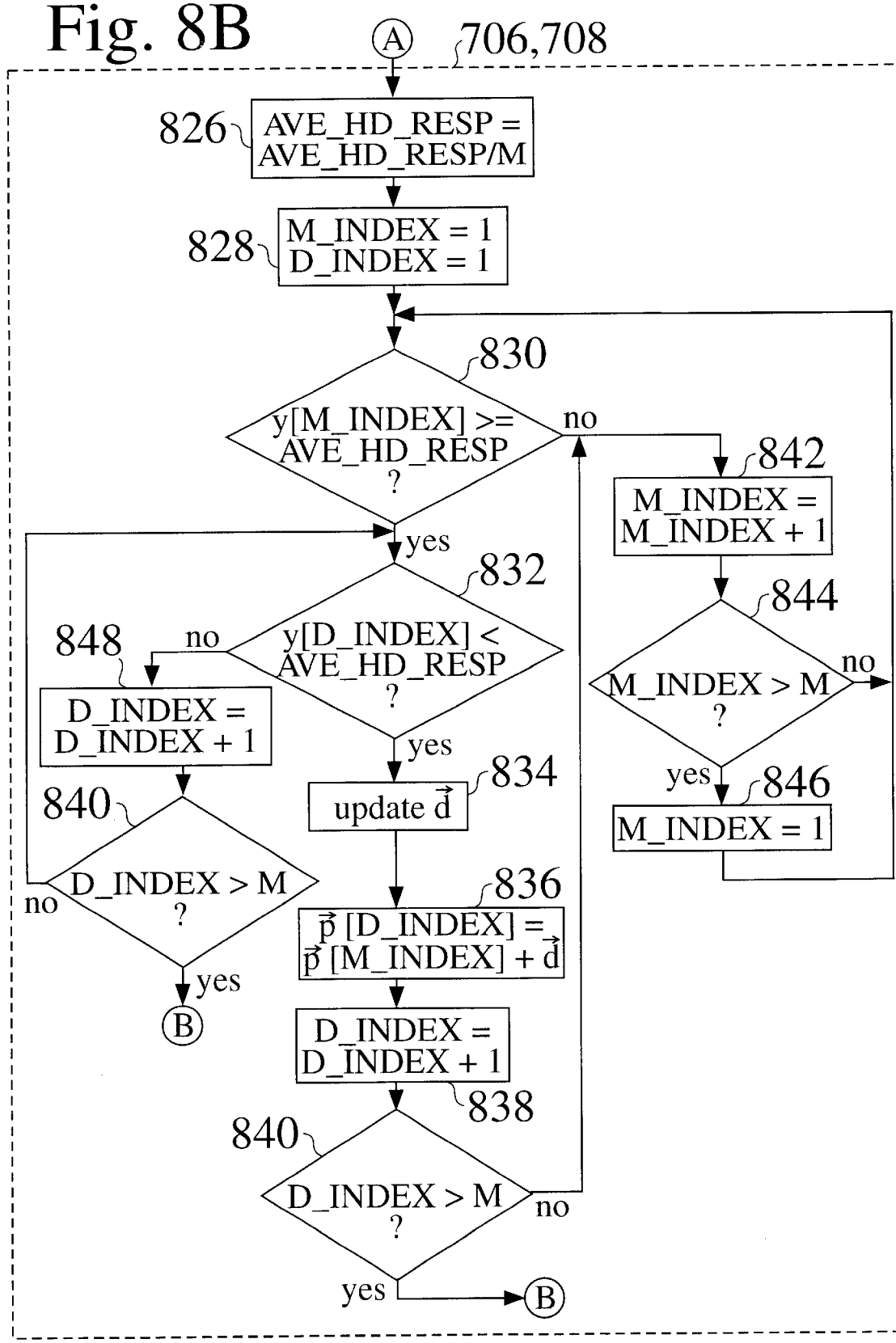

Referring now to the flow chart of FIGS. 8A and 8B, one way of implementing method 700 is shown using vector notation.

Referring first to FIG. 8A, method 700 starts at step 701 and proceeds immediately to step 702. At step 702, an initial plurality of sets of pacing parameters are determined. More specifically, $\vec{p}[n]$ is initialized for n=1 to M, where, M is the number of different sets of pacing parameters. $\vec{p}[n]$ is an N-dimensional vector containing the parameters of the n$^{th}$ set of pacing parameters, where N is the number of pacing parameters in each set.

For example, assume M=4 (i.e., there are four initial sets of pacing parameters) and N=2 (i.e., each set of pacing parameters includes two values). Exemplary sets of pacing parameters include: $\vec{p}[1]$=[100, 0]; $\vec{p}[2]$=[150, 10]; $\vec{p}[3]$=[180, 50]; and $\vec{p}[4]$=[90, 80], wherein, for example, the first value in each vector corresponds to AV delay, and the second value in each vector corresponds to RV-LV delay. If additional pacing parameters are being optimized, then the size of the vector is increased (and thus N is greater than 2), as would be apparent to one of ordinary skill in the art. If only one pacing parameter is being optimized, the N=1. Of course M can be greater than or less than four.

Next, at step 704, cardiac performance associated with each of the plurality of sets of pacing parameters is determined. In this embodiment, step 704 is broken into more detailed steps 802 through 824.

At step 802, n is set to 1, and an average cardiac performance value (also referred to as average hemodynamic response, and represented by AVE_HD_RESP) is set to 0.

Next, at step 804, a count (represented by TEST_COUNT) is set (i.e., initialized) to a predetermined number (represented by Ntest), such as four (4). The count represents the number of pulse amplitudes that will be measured when a heart is paced using a specific set of N pacing parameters $\vec{p}[n]$ (e.g. $\vec{p}[1]$). Also at step 804, a summation (represented by TEST_SUM) is cleared to zero.

At a step 806, the heart is paced with the current set of N pacing parameters $\vec{p}[n]$. Cardiac performance (also referred to as pulse amplitude measurements, cardiac function measurements, or hemodynamic response measurements) is preferably not measured following this first heart beat because such a measurement could be influenced by preload conditions generated by the previous pacing of the heart. In an alternative embodiment, more than the first beat are excluded from the measurement. At a step 808, the heart is again paced using the same set of N pacing parameters $\vec{p}[n]$ (e.g. $\vec{p}[1]$). The pulse amplitude r is then measured at a step 810. The pulse amplitude r can be obtained in a variety of ways, as discussed above.

At a step 812, the current pulse amplitude, obtained at step 810, is added to the running summation according to the equation TEST_SUM=TEST_SUM+r, where r represents the cardiac performance value determined at step 810. In other words, at step 812 pulse amplitudes are integrated.

At a step 814, the count is decremented according to the equation: TEST_COUNT=TEST_COUNT−1.

At a step 816, there is a determination of whether additional pulse amplitude measurements should be made while the heart is paced using the current set of N pacing parameters $\vec{p}[n]$. This can be answered by determining whether the count is equal to zero.

If additional pulse amplitude measurements should be made while the heart is paced using the same set of N pacing parameters $\vec{p}[n]$ (i.e., if the answer to step 816 is "NO"), then flow returns to step 808, as shown in FIG. 8. If the predetermined amount of pulse amplitude measurements have already been made while the heart is using the current set of N pacing parameters $\vec{p}[n]$, then flow continues to a step 818.

At step 818, $\vec{y}[n]$ is set to equal TEST_SUM, where y[n] is a scaler that contains the hemodynamic response (also referred to as the cardiac performance value) of the n$^{th}$ set of pacing parameters. This scaler will be used later on in method 800.

At a step 820, AVE_HD_RESP is updated according to the equation: AVE_HD_RESP=AVE_HD_RESP+TEST_SUM.

At a step 822, n is incremented according to the equation n=n+1.

At a step 824, there is a determination of whether there are additional sets of pacing parameters $\vec{p}[n]$ (where n=1 to M, as discussed above) at which the heart should be paced. This can be answered by determining whether n is greater than M (in the example, M=4).

If the heart is to be paced using additional sets of pacing parameters $\vec{p}[n]$ (i.e., if the answer to step 816 is "NO"), then flow returns to step 804, as shown in FIG. 8. In this manner, steps 804 through 822 are repeated for each of the plurality of sets of pacing parameters $\vec{p}[n]$, and the value AVE_HD_RESP is updated M times. If the heart has been paced using each of the plurality of sets of pacing parameters (i.e., for this example, sets $\vec{p}[1]$, $\vec{p}[2]$, $\vec{p}[3]$ and $\vec{p}[4]$), then flow continues to a step 826 of FIG. 8B.

Referring now to FIG. 8B, at step 826, the average cardiac performance value (also referred to as average pulse amplitude, or average hemdynamic response value) is determined according to the equation: AVE_HD_RESP=AVE_HD_RESP/M.

At a step 828, a mother index (M_INDEX) is initialized to 1, and a daughter index (D_INDEX) is also initialized to 1.

At a step 830, a cardiac performance value y[n] corresponding to one of the plurality of sets of pacing parameters $\vec{p}[n]$ is compared to the average cardiac performance value. More specifically, there is a determination of whether y[M_INDEX] is greater than or equal to the average cardiac function AVE_HD_RESP.

If y[M_INDEX] is greater than or equal to AVE_HD_RESP (i.e., if the answer to step 830 is "YES"), then flow goes to step 832, as shown in FIG. 8B. At step 832, there is a determination of whether y[D_INDEX] is less than the average cardiac function AVE_HD_RESP.

If y[D_INDEX] is less than AVE_HD_RESP, then flow goes to step 834, as shown. At step 834, an N dimensional increment or displacement vector $\vec{d}$ is updated. Vector $\vec{d}$ contains N "random" displacements, that are used (at a step 836) to produce randomized versions of those sets of cardiac pacing parameters that are greater than or equal to AVE_HD_RESP. An exemplary vector $\vec{d}$ is [12, −9]. Vector $\vec{d}$ can be updated in any number of different manners.

For example, in one embodiment, N random values can be created by selecting N values from a plurality of predefined (i.e., predetermined) numbers that have been stored. The random increment values are preferably within a predefined range, such that appropriate randomized versions of sets of pacing parameters can be produced. This simple embodiment would probably consume the least amount of power. Low power consumption is important if the determination is performed by an implantable device (e.g., pacing device 10).

In another embodiment, a random number generator is used to generate the random values. Such a random number generator can use mathematical algorithms to generate random or pseudorandom values. Alternatively, an element of hardware, such as a time of day clock, can be used to assist in generating random values. For example, a specific byte in the time of day clock can be sampled to produce random numbers when required. In still another embodiment, the random values can be created by performing an analog to digital conversion of a noisy channel. Of course, the use of other devices and/or methods for generating random values will be apparent to a person having skill in the relevant art and are within the spirit and scope of the present invention. Additionally, software, hardware, or combination of software and hardware can be used to generate the random values. For a more complete description of random number generation, see Chapters 7 and 10 of "Numerical Recipes in C, The Art of Scientific Computing, Second Edition" by Press et al., Cambridge University Press (1999), which are incorporated herein by reference. In each of these embodiments, the random increment values are preferably within a predefined range, such that appropriate randomized versions of sets of pacing parameters can be produced.

After vector $\vec{d}$ has been updated, a set of pacing parameters $\vec{p}[\text{D\_INDEX}]$ (corresponding to a cardiac performance value y[D\_INDEX] lower than the average cardiac performance value AVE\_HD\_RESP) is replaced with a randomized version of another set of pacing parameters $\vec{p}[\text{M\_INDEX}]$ (corresponding to a cardiac performance value y[M\_INDEX] greater than or equal to the average cardiac performance value AVE\_HD\_RESP). More specifically, at step 836, the set of pacing parameters $\vec{p}[\text{D\_INDEX}]$ is updated according to the equation: $\vec{p}[\text{D\_INDEX}]=\vec{p}[\text{M\_INDEX}]+\vec{d}$. For example, if $\vec{p}[\text{M\_INDEX}]=[100, 0]$ and updated vector $\vec{d}=[12, -9]$, then $\vec{p}[\text{D\_INDEX}]=[112, -9]$, which means AV delay is 112 msec and RV-LV delay is −9 msec. If a pacing parameter can be represented as a negative value, then the polarity of the pacing parameter indicates which portion of the heart is paced first. For example: an RV-LV delay of +9 msec indicates that the left ventricle is paced 9 msec after the pacing of the right ventricle; and an RV-LV delay of −9 msec indicates that the left ventricle is paced 9 msec prior to the pacing of the right ventricle.

At a step 838, D\_INDEX is incremented according to the equation D\_INDEX=D\_INDEX+1. Then, at a next step 840, there is a determination of whether there are additional cardiac performance values y[n] to compare to the average cardiac function value AVE\_HD\_RESP. This can be answered by determining whether D\_INDEX is greater than M (in the example, M=4).

If all of the cardiac performance values y[n] (where n=1 to M) have been compared to the average cardiac function AVE\_HD\_RESP, (i.e., if the answer to step 840 is "YES"), then flow returns to step 802 of FIG. 8A, as shown. If additional cardiac performance values should be compared to the average cardiac performance value AVE\_HD\_RESP, (i.e., if the answer to step 840 is "NO"), then flow goes to step 842, as shown. Flow will also go to step 842 if the answer to step 830, discussed above, is "NO".

As step 842, M\_INDEX is incremented according to the equation M\_INDEX=M\_INDEX+1. At a next step 844, the incremented M\_INDEX is compared to M. If M\_INDEX is not greater than M (i.e., if the answer to step 844 is "NO") then flow returns to step 830. If M\_INDEX is greater than M (i.e., if the answer to step 844 is "YES"), then M\_INDEX is reset to M=1 at a step 846, before flow returns to step 830, as shown.

Returning to step 832, if y[D\_INDEX] is not less than AVE\_HD\_RESP (i.e., if the answer to step 832 is "NO"), then flow goes to step 848, as shown. At step 848, D\_INDEX is incremented according to the equation D\_INDEX=D\_INDEX+1. At a next step 850, the incremented D\_INDEX is compared to M. If D\_INDEX is not greater than M (i.e., if the answer to step 844 is "NO") then flow returns to step 832. If D\_INDEX is greater than M (i.e., if the answer to step 850 is "YES"), then flow returns to step 802 as shown.

In the above discussed manner, steps 804 through 822 are repeated for each of the plurality of sets of pacing parameters $\vec{p}[n]$, and the value AVE\_HD\_RESP is updated M times. After the heart has been paced using each of the plurality of sets of pacing parameters (i.e., for this example, sets $\vec{p}[1]$, $\vec{p}[2]$, $\vec{p}[3]$ and $\vec{p}[4]$), then flow continues to step 826. Steps 802 though 824 are detailed sub-steps of step 704, according to an embodiment of the present invention.

At step 826 through 850, an average cardiac performance value is determined (at step 826), and the sets of pacing parameters associated with cardiac performance values less than the average are replace with randomized versions of the sets of pacing parameter associated with cardiac performance values greater than or equal to the average. Steps 826 through 850 are detailed sub-steps of steps 706 and 708, according to an embodiment of the present invention.

The previous description of the preferred embodiments is provided to enable any person skilled in the art to make or use the present invention. While the invention has been particularly shown and described with reference to preferred embodiments thereof, it will be understood by those skilled in the art that various changes in form and details may be made therein without departing from the spirit and scope of the invention.

Furthermore, embodiments of the present invention discussed above have been primarily described as methods with reference to flow charts. The present invention is also directed to devices (also referred to as apparatuses) that perform the features discussed above. For example, the present invention is also directed to a microprocessor (e.g., microprocessor 60) that performs the features of the present invention. Additionally, the present invention is also directed to an implantable device (e.g., pacing device 10) that includes a microprocessor for performing such features. Further, the present invention is also directed to systems that perform the features discussed above. Such a system can be, for example, an external processor in communications with a microprocessor of an implantable device.

Advantages of the Present Invention

There are a number of advantages of the present invention, some of which are discussed below.

The embodiments of the present invention track a plurality of sets of pacing parameters. Thus, in terms of parameters space, the present invention can track both global and local maximums. This is very useful if a patient's cardiac function is such that more than one region of parameter space provides good cardiac performance. This is also very useful where the best performing region of parameter space varies depending on the activity level or position of the patient, or some other factor. That is, because the present invention can track both global and local maximums, the present invention is more responsive (than algorithms that move a single point about a parameter space) where the best performing region of parameter space varies depending on the activity level or position of the patient.

The present invention enables automatic optimization of pacing parameters, thereby sparing electrophysiologists the time and effort of manually searching the parameter space for optimal settings. Further, by shortening the implant procedure, the present invention can be used to reduce risk to patients.

Different disease states require different parameter settings. For example, desynchronizing ventricular contraction improves cardiac performance in Hypertrophic Obstructive Cardiomyopathy, while in Dilated Cardiomyopathy cardiac performance is improved with synchrony. The embodiments of the present invention are general and adaptable, enabling adaption to either example.

Rapid parameter adjustment is necessary for on-the-fly pacing parameter optimization that allows an apparatus to respond to rapid changes in hemodynamics, as when a patient moves from supine to walking. Methods of parameter adjustment that require more than a minute or two preclude on-the-fly parameter optimization. The embodiments of the present invention are efficient and effective enough to allow for on-the-fly pacing optimization.

For patients whose baseline cardiac function is so compromised that pacing intervention is necessary, it is very important that the optimal parameter values are used. Ineffective approaches for determining pacing parameters may force compromises in the pacing parameters that are selected. The embodiments of the present invention enable optimal cardiac function to be obtained.

Further, the embodiments of the present invention allow the pacing parameters to track slowly changing hemodynamic variables, such as heart rate, blood pressure, and intrinsic contractility.

What is claimed is:

1. A method for determining pacing parameters associated with peak cardiac performance comprising the steps of:
    (a) determining a cardiac performance value for each of a plurality of sets of pacing parameters, wherein the plurality of sets comprises more than two sets of pacing parameters;
    (b) selecting at least two sets of pacing parameters from the plurality of sets of pacing parameters based on the cardiac performance values determined at step (a);
    (c) creating an updated plurality of sets of pacing parameters based on the at least two sets of pacing parameters selected at step (b); and
    (d) repeating steps (a) through (c), wherein each time steps (a) and (b) are repeated the updated plurality of sets of pacing parameters most recently created at step (c) are used.

2. The method of claim 1, wherein step (d) comprises repeating steps (a) through (c) until a criteria is satisfied.

3. The method of claim 2, further comprising, prior to step (d), determining an average cardiac performance value based on the cardiac performance values determined at step (a), and
    wherein step (d) comprises repeating steps (a) through (c) until a change in the average cardiac performance value is less than a predetermined amount.

4. The method of claim 1, wherein the updated plurality of sets of pacing parameters includes the at least two sets of pacing parameters selected at step (b).

5. The method of claim 1, wherein step (b) comprises selecting a predetermined percentage of the plurality of sets of pacing parameters based on the cardiac performance values determined at step (a).

6. The method of claim 1, wherein step (b) comprises:
    (b.1) selecting a set of pacing parameters corresponding to a maximum of the cardiac performance values determined at step (a); and
    (b.2) selecting each set of pacing parameters corresponding to a cardiac performance value within a predetermined range of the set of pacing parameters selected at step (b.1).

7. The method of claim 1, wherein step (b) comprises the steps of:
    (b.1.) determining an average cardiac performance value based on the cardiac performance values determined at step (a); and
    (b.2) selecting the at least two sets of pacing parameters from the plurality of sets of pacing parameters by selecting each set of pacing parameters corresponding to a cardiac performance value that is greater than the average cardiac performance value.

8. The method of claim 1, wherein step (b) comprises the steps of:
    (b.1) assigning each set a probability based on the cardiac performance values determined at step (a); and
    (b.2) selecting the at least two sets of pacing parameters from the plurality of sets of pacing parameters based on the probabilities assigned at step (b.1).

9. The method of claim 1, wherein at least some of the sets of pacing parameters created at step (c) are created by replacing a plurality of sets of pacing parameters not selected at step (b) with randomized versions of the at least two sets of pacing parameters selected at step (b).

10. The method of claim 1, wherein at least some of the sets of pacing parameters created at step (c) are created by:
    (c.1.) determining an average cardiac performance value based on the cardiac performance values determined at step (a); and
    (c.2) replacing each of the plurality of sets of pacing parameters corresponding to a cardiac performance value that is less than the average cardiac performance value with a randomized version of one of the plurality of sets of pacing parameters corresponding to a cardiac performance value that is greater than the average cardiac performance value.

11. The method of claim 10, wherein the updated plurality of sets of pacing parameters also includes each of the plurality of sets of pacing parameters corresponding to a cardiac performance value that is greater than the average cardiac performance value.

12. The method of claim 1, wherein step (c) comprises the steps of:
    (c.1.) creating at least two randomized versions of each of the at least two sets of pacing parameters selected at step (b); and
    (c.2) replacing each of the at least two sets of pacing parameters with the corresponding randomized versions created at step (c.1).

13. The method of claim 12, wherein step (c.1) comprises creating each of the randomized versions by:
    i. creating a set of random increment values; and
    ii. incrementing one of the at least two sets of pacing parameters based on the set of random increment values.

14. The method of claim 13, wherein step (c.1.i) comprises selecting a set of values from a plurality of predefined values, the selected values comprising the set of random increment values.

15. The method of claim 1, wherein each set of pacing parameters includes one pacing parameter.

16. The method of claim 1, wherein each set of pacing parameters includes at least two pacing parameters.

17. A device for improving cardiac performance associated with pacing parameters, the device comprising:
    a sensing circuit adapted to determine cardiac performance associated with a plurality of sets of pacing parameters, wherein the plurality of sets comprises more than two sets; and
    a processor adapted to
        select at least two sets of pacing parameters from the plurality of sets of pacing parameters based on the-cardiac performance determined by the sensing circuit, and
        create an updated plurality of sets of pacing parameters based on the at least two sets of selected pacing parameters, wherein the sensing circuit is adapted to determine the cardiac performance associated with the updated plurality of sets of pacing parameters, and the processor is adapted to select at least two further sets of pacing parameters from the updated plurality of sets of pacing parameters and create a further updated plurality of sets of pacing parameters.

18. The device of claim 17, wherein each updated plurality of sets of pacing parameters includes the at least two sets of pacing parameters upon which the updated plurality of sets of pacing parameters are based.

19. The device of claim 17, wherein the updated plurality of pacing parameters includes a predetermined percentage of the plurality of sets of pacing parameters based on the determined cardiac performance values.

20. The device of claim 17, wherein the updated plurality of pacing parameters includes a set of pacing parameters associated with a maximum of the determined cardiac performance values and each set of pacing parameters corresponding to a cardiac performance value within a predetermined range of the set of pacing parameters.

21. The device of claim 17, wherein the processor is adapted to determine an average cardiac performance value and select the at least two sets of pacing parameters based on the average cardiac performance value.

22. The device of claim 17, wherein the processor is adapted to assign each set a probability based on the cardiac performance values determined by the sensing circuit and select the at least two sets of pacing parameters from the plurality of sets of pacing parameters based on the assigned probabilities.

23. The device of claim 17, wherein the processor is adapted to create randomized versions of the at least two sets of pacing parameters, wherein the updated plurality of sets of pacing parameters includes the randomized versions.

24. The device of claim 17, wherein the processor is adapted to create randomized versions of the at least two sets of pacing parameters and to replace each of the plurality of sets of pacing parameters corresponding to a cardiac performance value that is less than the average cardiac performance value with a randomized version of one of the plurality of sets of pacing parameters corresponding to a cardiac performance value that is greater than the average cardiac performance value, wherein the updated plurality of sets of pacing parameters includes each randomized version.

25. The device of claim 24, wherein the updated plurality of sets of pacing parameters also includes each of the plurality of sets of pacing parameters corresponding to a cardiac performance value that is greater than the average cardiac performance value.

26. The device of claim 17, wherein the processor is adapted to create at least two randomized versions corresponding to each of the selected at least two sets of pacing parameters and to replace each of the at least two sets of pacing parameters with the corresponding randomized version.

27. The device of claim 26, wherein the processor is adapted to create each randomized version by creating a set of random increment values and incrementing one of the selected at least two sets of pacing parameters based on the set of random increment values.

28. The device of claim 27, wherein the processor is adapted to create each set of random increment values by selecting a set of values from a plurality of predefined values, the selected values comprising the set of random increment values.

29. The device of claim 17, wherein each set of pacing parameters includes one pacing parameter.

30. The device of claim 17, where each set of pacing parameters includes at least two pacing parameters.

31. A method for determining pacing parameters associated with peak cardiac performance, comprising the steps of:
    (a) determining a cardiac performance value for each of a plurality of sets of pacing parameters;
    (b) selecting at least one set of pacing parameters from the plurality of sets of pacing parameters based on the cardiac performance values determined at step (a);
    (c) determining an average cardiac performance value based on the cardiac performance values determined at step (a);
    (d) creating an updated plurality of sets of pacing parameters based on the at least one set of pacing parameters selected at step (b); and
    (e) repeating steps (a) through (d) until a change in the average cardiac performance value determined at step (c) is less than a predetermined amount, wherein each time steps (a) through (c) are repeated the updated plurality of sets of pacing parameters most recently created at step (d) are used.

32. The method of claim 31, wherein the updated plurality of sets of pacing parameters includes the at least one set of pacing parameters selected at step (b).

33. The method of claim 31, wherein each set of pacing parameters includes one pacing parameter.

34. The method of claim 31, wherein each set of pacing parameters includes at least two pacing parameters.

35. A method for determining pacing parameters associated with peak cardiac performance, comprising the steps of:
    (a) determining a cardiac performance value for each of a plurality of sets of pacing parameters;
    (b) determining an average cardiac performance value based on the cardiac performance values determined at step (a);
    (c) selecting each set of pacing parameters corresponding to a cardiac performance value that is greater than the average cardiac performance value;
    (d) creating an updated plurality of sets of pacing parameters based on the at least one set of pacing parameters selected at step (c); and
    (e) repeating steps (a) through (d), wherein each time steps (a) through (c) are repeated the updated plurality of sets of pacing parameters most recently created at step (d) are used.

36. The method of claim 35, wherein step (e) comprises repeating steps (a) through (d) until a criteria is satisfied.

37. The method of claim 36, wherein step (e) comprises repeating steps (a) through (d) until a change in the average cardiac performance value is less than a predetermined amount.

38. The method of claim 35, wherein each set of pacing parameters includes one pacing parameter.

39. The method of claim 35, wherein each set of pacing parameters includes at least two pacing parameters.

40. A method for determining pacing parameters associated with peak cardiac performance, comprising the steps of:
    (a) determining a cardiac performance value for each of a plurality of sets of pacing parameters;
    (b) assigning each set a probability based on the cardiac performance values determined at step (a);
    (c) selecting at least one set of pacing parameters from the plurality of sets of pacing parameters based on the probabilities assigned at step (b);
    (d) creating an updated plurality of sets of pacing parameters based on the at least one set of pacing parameters selected at step (c); and (e) repeating steps (a) through (d), wherein each time steps (a) through (c) are repeated the updated plurality of sets of pacing parameters most recently created at step (d) are used.

41. The method of claim 40, wherein step (e) comprises repeating steps (a) through (d) until a criteria is satisfied.

42. The method of claim 41, wherein step (e) comprises repeating steps (a) through (d) until a change in an average cardiac performance value is less than a predetermined amount.

43. A method for determining pacing parameters associated with peak cardiac performance, comprising the steps of:

(a) determining a cardiac performance value for each of a plurality of sets of pacing parameters;

(b) determining an average cardiac performance value based on the cardiac performance values determined at step (a);

(c) creating an updated plurality of sets of pacing parameters by replacing each of the plurality of sets of pacing parameters corresponding to a cardiac performance value that is less than the average cardiac performance value with a randomized version of one of the plurality of sets of pacing parameters corresponding to a cardiac performance value that is greater than the average cardiac performance value; and (d) repeating steps (a) through (c), wherein each time steps (a) and (b) are repeated the updated plurality of sets of pacing parameters most recently created at step (c) are used.

44. The method of claim 43, wherein the updated plurality of sets of pacing parameters also includes each of the plurality of sets of pacing parameters corresponding to a cardiac performance value that is greater than the average cardiac performance value.

45. The method of claim 43, wherein step (d) comprises repeating steps (a) through (c) until a criteria is satisfied.

46. The method of claim 45, wherein step (d) comprises repeating steps (a) through (c) until a change in the average cardiac performance value is less than a predetermined amount.

47. A method for determining pacing parameters associated with peak cardiac performance, comprising the steps of:

(a) determining a cardiac performance value for each of a plurality of sets of pacing parameters;

(b) selecting at least one set of pacing parameters from the plurality of sets of pacing parameters based on the cardiac performance values determined at step (a);

(c) creating an updated plurality of sets of pacing parameters by creating at least two randomized versions of each of the at least one set of pacing parameters selected at step (b), and replacing each of the at least one sets of pacing parameters with the corresponding randomized versions;

(d) repeating steps (a) through (c), wherein each time steps (a) and (b) are repeated the updated plurality of sets of pacing parameters most recently created at step (c) are used.

48. The method of claim 47, wherein step (c) includes creating each of the randomized versions by:

creating a set of random increment values; and incrementing one of the at least one set of pacing parameters selected at step (b), based on the set of random increment values.

49. The method of claim 48, wherein the step of creating a set of random increment values comprises selecting a set of values from a plurality of predefined values, the selected values comprising the set of random increment values.

50. The method of claim 47, wherein step (d) comprises repeating steps (a) through (c) until a criteria is satisfied.

51. The method of claim 50, wherein step (d) comprises repeating steps (a) through (c) until a change in an average cardiac performance value is less than a predetermined amount.

52. A device for improving cardiac performance associated with pacing parameters, the device comprising:

a sensing circuit adapted to determine cardiac performance associated with a plurality of sets of pacing parameters; and a processor adapted to determine an average cardiac performance value, select at least one set of pacing parameters based on the average cardiac performance value, and create an updated plurality of sets of pacing parameters based on the at least one set of selected pacing parameters, wherein the sensing circuit is adapted to determine the cardiac performance associated with the updated plurality of sets of pacing parameters, and the processor is adapted to select at least one set of pacing parameters from the updated plurality of sets of pacing parameters and create a further updated plurality of sets of pacing parameters.

53. A device for improving cardiac performance associated with pacing parameters, the device comprising:

a sensing circuit adapted to determine cardiac performance associated with a plurality of sets of pacing parameters; and a processor adapted to assign each set a probability based on the cardiac performance values determined by the sensing circuit and select at least one set of pacing parameters from the plurality of sets of pacing parameters based on the assigned probabilities, wherein the sensing circuit is adapted to determine the cardiac performance associated with the updated plurality of sets of pacing parameters, and the processor is adapted to select at least one set of pacing parameters from the updated plurality of sets of pacing parameters and create a further updated plurality of sets of pacing parameters.

54. A device for improving cardiac performance associated with pacing parameters, the device comprising:

a sensing circuit adapted to determine cardiac performance associated with a plurality of sets of pacing parameters; and a processor adapted to determine an average cardiac performance value based on the cardiac performance values determined by the sensing circuit, and create an updated plurality of sets of pacing parameters by replacing each of the plurality of sets of pacing parameters corresponding to a cardiac performance value that is less than the average cardiac performance value with a randomized version of one of the plurality of sets of pacing parameters corresponding to a cardiac performance value that is greater than the average cardiac performance value;

wherein the sensing circuit is adapted to determine the cardiac performance associated with the updated plurality of sets of pacing parameters, and the processor is adapted to create a further updated plurality of sets of pacing parameters.

55. The device of claim 54, wherein the updated plurality of sets of pacing parameters also includes each. of the plurality of sets of pacing parameters corresponding to a cardiac performance value that is greater than the average cardiac performance value.

56. A device for improving cardiac performance associated with pacing parameters, the device comprising:

a sensing circuit adapted to determine cardiac performance associated with a plurality of sets of pacing parameters; and a processor adapted to select at least one set of pacing parameters from the plurality of sets of pacing parameters based on the cardiac performance determined by the sensing circuit, and create at least two randomized versions corresponding to each of the selected at least one set of pacing parameters and to replace each of the at least one set of pacing parameters with the corresponding randomized versions to thereby produce an updated plurality of sets of pacing parameters;

wherein the sensing circuit is adapted to determine the cardiac performance associated with the updated plurality of sets of pacing parameters, and the processor is adapted to select at least one set of pacing parameters from the updated plurality of sets of pacing parameters and create a further updated plurality of sets of pacing parameters.

57. The device of claim 56, wherein the processor is adapted to create each randomized version by creating a set of random increment values and to increment one of the selected at least one set of pacing parameters based on the set of random increment values.

58. The device of claim 57, wherein the processor is adapted to create each set of random increment values by selecting a set of values from a plurality of predefined values, the selected values comprising the set of random increment values.

59. A method for determining pacing parameters associated with peak cardiac performance comprising the steps of:

(a) determining a cardiac performance value for each of a plurality of sets of pacing parameters, wherein each set comprises at least an AV delay pacing parameter and an RV-LV delay pacing parameter;

(b) selecting at least one set of pacing parameters from the plurality of sets of pacing parameters based on the cardiac performance values determined at step (a);

(c) creating an updated plurality of sets of pacing parameters based on the at least one set of pacing parameters selected at step (b); and (d) repeating steps (a) through (c), wherein each time steps (a) and (b) are repeated the updated plurality of sets of pacing parameters most recently created at step (c) are used.

* * * * *